United States Patent [19]

Goodall et al.

[11] Patent Number: 5,204,095
[45] Date of Patent: Apr. 20, 1993

[54] MONOCLONAL ANTIBODIES AGAINST HEPATITIS B VIRUS

[75] Inventors: Alison H. Goodall, Buntingford; George Janossy, Harrow; Howard C. Thomas, London, all of England

[73] Assignee: National Research Development Corporation, London, England

[21] Appl. No.: 554,985

[22] Filed: Jul. 17, 1990

Related U.S. Application Data

[63] Continuation of Ser. No. 873,289, Jun. 5, 1986, abandoned, which is a continuation of Ser. No. 293,243, Aug. 17, 1981, abandoned, which is a continuation of Ser. No. 252,069, Apr. 8, 1981, abandoned.

[30] Foreign Application Priority Data

Apr. 9, 1980 [GB] United Kingdom ............... 8011697
Jun. 26, 1981 [GB] United Kingdom ............... 8119762

[51] Int. Cl.$^5$ .................... A61K 39/42; A61K 39/44
[52] U.S. Cl. ..................................... 424/86; 424/89; 435/70.21; 435/172.2; 435/240.27; 435/5; 435/7.9; 436/518; 436/548; 436/531; 436/820; 530/388.3
[58] Field of Search ........................ 530/387, 388.3; 435/70.21, 70.1, 172.2, 240.27, 810, 5, 7.9; 436/518, 548, 528, 531, 533, 808, 810, 820; 424/85.8, 86, 88, 89

[56] References Cited

U.S. PATENT DOCUMENTS 4,172,124 10/1979 Koprowski et al.
4,196,265 4/1980 Koprowski et al.
4,271,145 6/1981 Wands et al. ................. 424/85
4,491,632 1/1985 Wands et al.

FOREIGN PATENT DOCUMENTS 0038642 10/1981 European Pat. Off. ............ 435/240
2000186 1/1979 United Kingdom.

OTHER PUBLICATIONS

*Proc. Nat. Acad. Sci* vol. 75i pp. 3938–3942 (1978) Wiktor et al.
*Proc. Nat. Acad. Sci* vol. 75; pp. 1510–1514 (1978) Gerhard et al.
The Lancet (Jun. 11, 1977) pp. 1242–1243 Spin-off from Cell Fusion.
"The Production of a Monoclonal Antibody to HBs Antigen and its use in the Detection and Immunopathology of Hepatitis B Virus Infection" (1980) Goodall et al. (Paris) Abstract 19.2.09.
Transfusion (Philadelphia) 19 No. 5, p. 637 (Sep./Oct. 1979) Shih et al "Production of Monoclonal Antibodies Against Hepatitis B Surface Antigen by Somatic Cell Hybrids".
Gastroenterology 77 No. 5 P.A46 (1979) Wands et al "Production and characterisation of Monoclonal Antibodies to Hepatitis B surface antigen (HBsAg) by cellular hybridisation".
Federation Proceedings 39 No. 3, p. 929, point 3484 (Mar. 1, 1980) Present et al "Characterization of murine hybridoma antibodies to Hepatitis B surface antigenic determinants".
Gastroenterology 79, No. 5 p. 1063 (part 2, Nov. 1980) Wands et al "Immunodiagnosis of Hepatitis B by high affinity monoclonal anti–HB antibodies".
Gastroenterology 79, No. 5 p. 1063 (part 2, Nov. 1980) Wands et al "Identification of epitopes on HB Ag polypeptides by analysis with monoclonal anti–Hbs antibodies".
Wands, J. R. et al, Proc. Natl. Acad. Sci, USA, vol. 78(2), pp. 1214–1218 (Feb. 1981).
Wands, J. R. et al, Proc. Natl. Acad. Sci, USA, vol. 79, pp. 1277–1281 (Feb. 1982).

*Primary Examiner*—Sam Rosen
*Attorney, Agent, or Firm*—Nixon & Vanderhye

[57] ABSTRACT

The new hybridoma cell lines RF-HBs-1, RF-HBs-2 and RF-HBs-4 each secrete a monoclonal antibody to hepatitis B surface antigen. The production of the antibodies may be carried out in vitro by culturing one of the cell lines or in vivo by establishing one of the cell lines as an ascites tumour in a mouse and isolating antibodies from the ascites fluid or from the serum. The antibodies have therapeutic, preventative and diagnostic uses in respect of hepatitis B virus infections and can be used to purify hepatitis B surface antigen. The relative specificities of the three monoclonal antibodies make them particularly useful in radiometric assay techniques employing specific combinations of the antibodies in solid phase.

24 Claims, No Drawings

MONOCLONAL ANTIBODIES AGAINST HEPATITIS B VIRUS

This is a continuation of application Ser. No. 06/873,289, filed Jun. 5, 1986, now abandoned, which is a continuation of U.S. Ser. No. 06/293,243, filed Aug. 17, 1981, now abandoned, which is continuation of U.S. Ser. No. 06/252,069, filed Apr. 8, 1981, now abandoned.

The present invention relates to monoclonal antibodies to hepatitis B surface antigen (HBsAg) which are secreted by new hybridoma cell lines, and particularly the use of these monoclonal antibodies in assay systems for hepatitis B virus infections.

The development of new cell lines that can be continuously subcultured has been an important area of research in recent years. One particular application for such cell lines lies in the production of antibodies and the introduction of somatic cell hybridisation (i.e. cell fusion) has provided a research tool which enables production of pure, monoclonal antibodies. By fusing antibody secreting cells with meloma cells and cloning the resulting antibody-secreting hybrids in tissue culture, it has been found possible to produce and select a stable hybrid monoclonal cell line that is capable of secreting a particular antibody. It is thus possible to ensure the production of pure, monospecific antibodies since, in the monoclonal cell line, they arise from one original antibody secreting cell.

This ability to produce pure, monospecific antibodies is clearly of great utility for accurate screening, purification of the antigen and in therapeutic/preventative applications and the present invention is directed towards the use of these techniques in connection with hepatitis B virus infections.

The diagnosis of acute and chronic hepatitis B infection is dependent upon the detection of HBs antigen in a patient's blood. This has generally been achieved by a radioimmunoassay utilising rabbit or horse anti HBs serum absorbed onto polystyrene beads. The HBs antigen in the patient's serum binds to the solid phase antibody and can then be detected by a further application of radiolabelled anti-HBs. Another technique for detecting HBs-Ag in the liver employs double-layer immunofluorescence. These techniques do, however, involve a primary procedure where the antiserum is raised in rabbits and the antibodies purified by expensive and time-consuming affinity chromatography.

The use of radioimmunoassay techniques for detecting HBs antigen is well established in connection with blood transfusion services but has not been extensively implemented for screening hospital patients in general. Apart from the obvious desirability of this for reducing risk of infection within the hospital, the identification in particular of obstetric patients who are carriers of hepatitis virus can be of great importance since identification of the carrier mother may allow administration of hyperimmune globulin to the infant shortly after birth and thus considerably reduce the risk of its developing hepatitis and of becoming a chronic carrier.

Any increase in the screening for hepatitis B virus infection and in the possible treatment of the disease will demand large quantities of readily available, high quality anti-HBs serum. Three new hybrid monoclonal cell lines have now been found and designated RF-HBs-1, RF-HBs-2 and RF-HBs-4; they have been shown to be stable in culture and each secretes a monoclonal antibody to hepatitis B surface antigen. Moreover, these cell lines are capable of storage in, and recovery from, liquid nitrogen and thus provide a readily available supply of pure monospecific antibodies to hepatitis B surface antigen.

The present invention accordingly provides a monoclonal antibody to hepatitis B surface antigen which is secreted by the hybridoma cell line RF-HBs-1, RF-HBs-2 or RF-HBs-4. Desirably, the monoclonal antibodies are in substantially pure form free from other immunological material. The present invention also provides a composition containing one or more of these monoclonal antibodies and a suitable carrier or diluent.

The monoclonal (and hence monospecific) antibodies of the present invention may be recovered from a culture supernatant or from mouse ascites fluid or serum as is indicated hereinafter. They each show activity against HBs-Ag and are precipitated by rabbit antiserum raised against mouse $IgG_1$ heavy chain and against mouse K light chain but not by rabbit anti-serum to mouse $IgG_{2a}$, $IgG_{2b}$, IgM or IgA or to mouse $\lambda$ light chains. Thus, each monoclonal antibody is an $IgG_{1(k)}$ mouse immunoglobulin that reacts with major subtypes of the HBsAg (ad and ay) and can be produced by culturing the cell line RF-HBs-1, RF-HBs-2 or RF-HBs-4.

The cell lines RF HBs-1, -2 and -4 are hybridoma cell lines which have been produced by fusing spleen cells from Balb/c mice, previously immunized with concentrated hepatitis B surface antigen (HBsAg), with the HAT-sensitive mouse myeloma cell line (P3-NS1/1 Ag4-1), according to the methods of Kohler and Milstein (Eur. J. Immunol. 6, 292 (1976)). By cloning procedures using three of these fused cell lines, the hybridoma monoclonal cell lines designated RF-HBs-1, RF-HBs-2 and RF-HBs-4, respectively, have been isolated.

The cell lines RF-HBs-1, -2 and -4 each appear as a fairly uniform population of cells which morphologically resemble the parent NS1 myeloma in both size and shape having a mean size of 13 $\mu$m. They each appear spherical in culture and have a centrally located nucleus with a large cytoplasmic area, equal to or greater than the nuclear volume. RF-HBs-1 differs from the parent line in that although, like the parental line, it grows partially attached to a solid substratum, e.g. glass or plastic, it can be detached from this surface by vigorous agitation and does not require trypsinisation or treatment with EGTA. It also grows as a suspension culture in stirrer culture vessels. RF-HBs-2 grows partially attached to a substratum and requires trypsinisation for sub-culture, while RF-HBs-4 grows as a static suspension culture with passaging being effected by dilution of the culture e.g 1:10. The cells have doubling times of 14.6 hours, 10.7 hours and 9.2 hours, respectively, and will grow in RPMI-FCS medium (see below) each requiring feeding at 2-3 day intervals and sub-culturing at 2-3 day intervals for RF-HBs-1, 3-4 day intervals for RF-HBs-2 and 2-3 day intervals for RF-HBs-4.

The hybridoma cell lines RF-HBs-1, -2 and -4 each secrete an antibody of the present invention and the cell lines have each continued to secrete antibody for at least three months in continuous culture.

Accordingly, the present invention also provides each of the hybridoma cell lines designated RF-HBs-1, -2 and -4 which secrete monoclonal antibodies to hepatitis B surface antigen, the cell lines preferably being in substantially pure form free from other cellular material, and compositions containing one or more of these cell lines, together with a nutrient medium capable of maintaining the cell line(s). An appropriate medium contains a source of carbon, a source of nitrogen and if desired, vitamins, and/or inorganic salts, and an example of such a medium is RPMI-1640 supplemented with foetal calf serum e.g. RPMI-FCS (see below).

In the preparation of the hybridoma cell line RF-HBs-1, Balb/c mice were immunised by intraperitoneal injection of 0.2 ml of purified HBs antigen diluted 1:1 with complete Freunds adjuvant (CFA) at a final antigen concentration of 0.7 mg/ml. (The HBs antigen (subtype adw) used was purified from HBs antigen-positive serum by caesium chloride density gradient centrifugation). Four weeks later, the mice were boosted with a further 0.2 ml injection of the HBs antigen/CFA mixture. Six weeks later the mouse that gave the highest serum titre of antibody to HBs antigen, as determined by solid phase radioimmunoassay, was boosted with a further 0.2 ml I.P. injection of HBs antigen in CFA, and killed 5 days after this final boost and the spleen removed.

The spleen was teased in RPMI-1640 medium, supplemented with 10% v/v foetal calf serum, 2 mM glutamine and 100 IU each of penicillin and streptomycin (RPMI-FCS) at 37° C., pH 7.2 and sodium bicarbonate concentration of 2 g/l, and the resultant suspension was passed several times, gently, in and out of a sterile 10 ml syringe. The single cell suspension was decanted from the few residual lumps of unseparated spleen and the cells were washed twice in serum-free RPMI-1640, centrifuging at 1500 g for 5 minutes. The washed cell pellet was resuspended in RPMI-1640.

A semi-confluent culture of mouse myeloma cells $P_3$-NS1/1-Ag4-1 (i.e. a culture of cells in an active stage of growth having been maintained in continuous culture at 37° C. in RPMI-1640 medium supplemented with 10% (v/v) foetal calf serum, 2 mM glutamine, 100 IU of penicillin and 100 $\mu$g streptomycin and $2 \times 10^{-5}$M 8-thioguanine buffered with bicarbonate/$CO_2$) were detached from their culture vessel by mild trypsinisation and washed twice in serum-free RPMI-1640 by centrifugation at 400 g. The washed cells were resuspended in RPMI-1640 and counted.

In order to effect hybridisation, the total spleen cell population was mixed with the myeloma cells in a round-bottomed, sterile, 10 ml centrifuge tube in a ratio of 10 to 1 spleen cells to myeloma cells, and co-pelleted by centrifugation at 1500 g. After removal of the supernatant, 1 ml of a 40% (w/w) solution of polyethylene glycol (PEG) 1500 in RPMI-1640, that had been prewarmed to 37° C., was added to the cell pellet and gently mixed with the cells. The cell-PEG mixture was incubated at 37° C. for exactly 7 minutes and then the PEG solution was gradually diluted off the cells by repeated addition of equal volumes of RPMI-1640, until the PEG concentration was below 0.5% (w/w). The suspension was centrifuged at 1500 g and the cell pellet gently resuspended and washed twice in serum-free RPMI-1640, centrifuging at 1000 g. The washed cell pellet was gently resuspended in 1 ml of RPMI-FCS, and incubated for two hours at 37° C. and the cells were then distributed, at $1 \times 10^6$ cells/ml in RPMI-FCS, into $24 \times 2$ ml multiwell tissue culture plates and cultured at 37° C. in a 5% $CO_2$/95% air atmosphere.

Twenty-four hours after fusion, half of the culture medium in each flask was replaced by HAT medium (RPMI-FCS supplemented with $1 \times 10^{-4}$M hypoxanthine, $4 \times 10^{-7}$M aminopterin and $1.6 \times 10^{-5}$ thymidine). The cultures were supplemented with fresh HAT medium, in this way, every day for the first 3 days and at 2-3 day intervals thereafter, to ensure selection of hybrid cells with the ability to grow in HAT medium.

The HAT medium was replaced by HT medium (RPMI-FCS + hypoxanthine and thymidine) in stages, beginning at day 40 after fusion and then adapted to growth in RPMI-FCS at day 52 after fusion.

Supernatants from the hybrid cultures were assayed for antibody to HBs antigen as soon as the wells showed growth of more than 100 cells. Only one culture well contained antibody-producing cells though other culture wells did contain viable hybrid cells.

The antibody producing hybrid cells from this one culture well were then cloned, initially by limiting dilution of the original cultures onto a feeder layer of spleen cells from a non-immunised Balb/c mouse, growing the hybrids in $96 \times 0.2$ ml cluster dishes in RPMI-FCS. Growth was produced in 16 wells that had been confirmed as containing only one hybrid cell at the start of the cloning schedule, and from these the cell line RF-HBs-1 was selected as providing a stable hybrid cell line secreting monoclonal antibodies to HBs antigen. This clone of cells has subsequently been recloned twice with the result of 100% antibody-producing clones.

In the preparation of the hybridoma cell line RF-HBs-2, six week old male, Balb/c mice were immunised with affinity-purified HBsAg (subtype ay) by intraperitoneal injections of 20 $\mu$g HBsAg in complete Freund's adjuvant (CFA; 0.2 ml per mouse). 2 Weeks later the mice were boosted with a further I.P. injection of 5 $\mu$g of HBsAg in CFA and the mouse that gave the highest titre of serum anti-HBsAg was boosted after a further 2 weeks by I.P. injection of 5 $\mu$g HBsAg in saline. 3 Days after the final boost the mouse was killed and the spleen removed. At this time the mouse had a serum anti HBsAg titre of 1:1000. (All anti-HBsAg measurements were determined by "AUSAB" radio-immunoassay (Abbott Laboratories) and antibody titres in this specification are given as the dilution that gives 50% of maximum binding).

The spleen cells from the immunised mouse were dissociated in RPMI-FCS at 37° C., pH 7.2 and sodium bicarbonate concentration of 2.0 g/l. The total spleen cell population was washed twice with serum-free medium (RPMI-1640) and mixed with the $P_3$-NS1/1-Ag4-1 mouse myeloma cells in a 10:1 (spleen cell:myeloma cell) ratio, pelleted and resuspended in 1 ml of 40% (w/w) polyethylene glycol (PEG) 1500 in RPMI-1640. Following a 7 minute incubation, the PEG was gently diluted from the cells by gradual addition of RPMI-1640. The cell suspension was washed once in RPMI-1640, centrifuged at 1500 g, and then incubated for 2 hours in 3 ml RPMI-FCS, after which the cells were plated into 2 ml culture wells at $2 \times 10^6$ cells/well. All operations were carried out at 37° C.

The cells were cultured overnight at 37° C. in RPMI-FCS in a 5% $CO_2$/95% air atmosphere, and then half of the medium in each culture well was replaced by HAT medium. The cultures were fed with fresh HAT medium, in this way, at one day intervals for the first 3 days and then at 2-3 day intervals thereafter, to select the hybrid cells from the HAT-sensitive myeloma cells. Approximately 3 weeks after fusion the hybrid cells were reintroduced to RPMI-FCS medium.

Of the 168 wells originally plated, 148 produced growth of hybrid cells, of which 4 showed production of anti-HBsAg activity. Of these 4, one hybrid culture that appeared 20 days after fusion has continued to produce antibody to HBsAg. This cell line has been cloned 3 times and one of the resultant antibody-secreting clones is the cell line designated RF-HBs-2.

In the preparation of the hybridoma cell line RF-HBs-4, six week old male, Balb/c mice were immunised with affinity-purified HBsAg (subtype ad) by intraperitoneal injections of 20 $\mu$g HBs-Ag in complete Freund's adjuvant (CFA; 0.2 ml per mouse). 3 Weeks later the mice were boosted with a further I.P. injection of 5 $\mu$g HBsAg in CFA and the mouse which gave the highest titre of serum anti-HBsAg was boosted after a further 10 days by I.P. injection of 5 $\mu$g HBsAg in saline. 5 Days after the final boost the mouse was killed and the spleen removed. At this time the mouse had a serum anti-HBsAg titre of 1:7000.

The procedure was then identical with that used in preparing the hybridoma cell line RF-HBs-2 from the dissociation of the spleen cells from the immunised mouse up to the plating at 37° C. of the hybridised cells into 2 ml culture wells at $2 \times 10^6$ cells/well. Culture and selection conditions were also identical with that procedure and, of the 144 wells originally plated, 129 produced growth of hybrid cells, of which 5 showed production of anti-HBsAg activity. Of these 5, one hybrid culture that appeared 15 days after fusion has continued to produce antibody to HBsAg. This cell line has been cloned 3 times and one of the resultant antibody-secreting clones is the cell line designated RF-HBs-4.

A further aspect of the present invention resides in a process for the propagation of the hybridoma cell line RF-HBs-1, RF-HBs-2 or RF-HBs-4 which comprises culturing the cells of one of these cell lines in a nutrient culture medium therefor. This method of propagation also represents a means of producing the antibodies of the invention which may be separated from the culture medium. An appropriate nutrient culture medium for the cells of the present invention contains a source of carbon, a source of nitrogen and, if desired, vitamins and/or inorganic salts, and is, for example, RPMI-1640 supplemented with foetal calf serum e.g. in an amount of about 10% by weight based on the culture medium. RPMI-FCS described above is particularly suitable. When growing the cells, a suitable initial concentration is $1 \times 10^5$ cells/ml for RF-HBs-1, $1 \times 10^5$ cells/ml for RF-HBs-2 and $2 \times 10^5$ cells/ml for RF-HBs-4. These concentrations should desirably not be allowed to exceed $1 \times 10^6$ cells/ml, $2 \times 10^6$ cells/ml and $3 \times 10^6$ cells/ml respectively.

In addition to culturing the cell lines of the present invention in a nutrient medium, it is also possible to implant each one of the cell lines into a mouse to establish an ascites tumour; this is generally carried out by intraperitoneal injection of, for example, $4 \times 10^5 - 1 \times 10^6$ cells per mouse, into pristane (2,6,10,14-tetramethyl pentadecane)-primed, Balb/c mice. Establishment of an ascites tumour may also be achieved in non pristane-primed mice in which case, when propagating RF-HBs-1 cells $1 \times 10^6 - 2 \times 10^6$ cells per mouse should be injected, while the minimum number of cells per mouse for RF-HBs-2 and RF-HBs-4 is $4-5 \times 10^5$. The cell lines may also be grown as a solid tumour by subcutaneous injection.

The monoclonal antibodies secreted by the hybridoma may then be recovered from the ascites fluid or from the mouse serum and this process of both propagating the cell lines and producing the antibodies represents a still further aspect of the present invention. This means of obtaining the monoclonal antibodies does offer the advantage that the yield of antibodies may, for example, be as much as 10-fold higher than the yield obtainable from the bulk culture of the cells. It will normally take about 2 to 3 weeks for the cells to grow up in the mice.

The antibodies of the invention may be used unpurified from such sources as described above, or, preferably, are subjected to purification before use. For example, antibodies to be coupled to sepharose for use in affinity chromatography are generally purified by ammonium sulphate precipitation, while antibodies to be iodinated or biotin-conjugated are generally subjected to Protein A-purification.

The hybridoma cells of the invention may be stored in FCS-supplemented RPMI-1640 medium containing say 20% FCS by freezing in liquid nitrogen at, for example, $5 \times 10^6$ cells/ml or higher using 10% dimethylsulphoxide as cryoprotectant. The freezing rate is preferably controlled between $+40°$ C. and $-100°$ C. at $1°-2°$ C./minute and the frozen cells can be stored below $-100°$ C. e.g. at $-170°$ C. in a liquid nitrogen refrigerator.

The monospecific antibodies produced by cell lines RF-HBs-1, -2 and -4 are of particular value in providing accurate screening tests for patients infected by hepatitis B virus. These antibodies can be used in assay systems, employing for example, immunofluorescent microscopy or immuno-electron microscopy, in detecting the presence of HBsAg in cellular material or in serum. Quantitative assays may be carried out by solid phase radiometric assay, and RF-HBs-1 antibody is useful in this respect since it recognises an antigenic epitope that appears with relatively high frequency on the HBsAg molecule. However, particularly useful solid-phase radiometric assay systems in accordance with this invention employ combinations of the monoclonal antibodies.

The antibodies produced by the RF-HBs-2 and RF-HBs-4 cell lines, which are of high affinity for epitopes occurring with low frequency on HBs-Ag, may be used together as a solid-phase, in a radiometric assay for the detection of HBs-Ag, either alone or with RF-HBs-1 antibody as illustrated in the following Examples. The use of a solid-phase comprising RF-HBs-2 and RF-HBs-4 antibodies alone is applicable to a one-stage radioassay for HBsAg (Example 7 below illustrates how these two antibodies between them recognise all HBs-Ag molecules), whereas the addition of RF-HBs-1 antibody to the solid-phase acts as an additional safeguard when used in a two-stage assay, since RF-HBs-1 antibody, although of lower affinity for HBsAg then the other two monoclonal antibodies, itself recognises all HBsAg molecules, thus ensuring anchorage of the antigen to the solid-phase. In solid-phaseradiometric assay systems employing these monoclonal antibodies, the RF-HBs-1 antibody is preferably used as radiolabelled tracer, not only because this antibody recognises all HBsAg molecules but also, due to the fact that it recognises an epitope of HBsAg that occurs in high frequency on the molecule, gives a higher number of counts in the assay than do the other two antibodies, either alone or in combination. Support for the use of all three monoclonal antibodies in a radiometric assay is provided by competitive binding studies (see Example 4 below) which illustrate that neither RF-HBs-2 nor RF-HBs-4 antibodies inhibit the binding of the RF-HBs-1 antibody to HBsAg.

Thus, a preferred diagnostic method in accordance with the invention comprises incubating a serum sample taken from a human or animal either in a two-stage assay with RF-HBs-1, RF-HBs-2 and RF-HBs-4 antibodies in the solid-phase, washing the solid phase and incubating it with radiolabelled RF-HBs-1 antibody as tracer; or in a one-stage assay with RF-HBs-2 and RF-HBs-4 antibodies in the solid-phase and radiolabelled RF-HBs-1 antibody as tracer. In each of these assay systems, the solid phase preferably comprises a plastics or glass substrate on which the antibodies are coated; the substrate is particularly preferred in the form of beads, sticks or tubes, e.g. of polystyrene. The present invention also provides these coated substrates e.g. beads, and a diagnostic kit comprising a first container which contains a plastics or glass substrate such as beads, sticks or tubes coated with RF-HBs-1, RF-HBs-2 and RF-HBs-4 antibodies or with RF-HBs-2 and RF-HBs-4 antibodies and a second container which contains RF-HBs-1 antibody to which a radiolabel has been attached. (In these assay systems, instead of employing RF-HBs-1 antibody with the other two monoclonals of the invention, it is possible to use RF-HBs-1 antibody with one or more other monoclonal antibodies which recognise HBs-Ag.)

Alternative assay methods, in accordance with the invention, may, instead of employing a radiolabel, employ e.g. an enzyme-label or a biotin-label which will generally be linked to the RF-HBs-1 antibody. Further, it is also possible to use one or more of the antibodies of the invention in a haemagglutination assay for HBs-Ag.

One or more of the monoclonal antibodies of this invention coupled to a solid-phase such as cyanogen bromide-activated Sepharose 4B (CnBr-S4B; Pharmacia Fine Chemicals, Uppsala, Sweden), can also be used to remove HBs-Ag e.g. from human or animal material, either for the purpose of preparing HBs-Ag in a purified form for use in preparing vaccines or for the removal of HBs-Ag from material to be given to patients. Thus, the present invention also provides a method of isolating hepatitis B surface antigen from a biological sample which comprises contacting the biological sample with RF-HBs-1, RF-HBs-2 and/or RF-HBs-4 antibodies in the solid phase to cause binding of antigen to antibody and subsequently separating the desired purified material from the solid phase.

The monoclonal antibodies to HBsAg of the present invention are also of value, particularly the antibodies from RF-HBs-1, in clinical applications as an anti-viral agent where antibody is to be administered directly to patients. The monoclonal antibodies may have a role in the treatment of patients carrying the hepatitis B virus and may neutralise the infectivity of the virus by inhibiting its combination with the receptor site on cells and also enhance the phagocytosis and intracellular digestion of the viruses. Potentially the use of these monoclonal antibodies in this context as a substitute for hyper-immune gamma globulin may avoid giving large amounts of non-specific immunoglobulin along with the small amounts of the specific antibody, which is the case with conventional serum. Each antibody, particularly that from RF-HBs-1, may also serve to break tolerance in HBV carriers by binding to the HBs-Ag and making it more immunogenic.

A further aspect of the present invention is thus a pharmaceutical composition comprising one or more of the monoclonal antibodies of the present invention and a pharmaceutically acceptable inert carrier or diluent.

For therapeutic and/or preventative use, the composition may be in solid or liquid form and presented in a conventional manner for parenteral or oral application. Thus, the compositions may be in the form of injectable solutions or in the form of tablets, capsules, solutions or suspensions.

The monoclonal cell lines RF-HBs-1, RF-HBs-2 and RF-HBs-4 have been deposited with the Collection Nationale de Cultures de Microorganismes (C.N.C.M.) at the Institut Pasteur, Paris on Mar. 26, 1980, May 20, 1981 and May 20, 1981, respectively, and have been given the accession numbers I-117, I-150 and I-151 respectively.

The present invention will now be further illustrated by the following Examples.

EXAMPLE 1

In Vitro Culturing of Cell Line RF-HBs-1

RF-HBs-1 cells were seeded at $1 \times 10^5$ cells/ml in RPMI-1640 medium supplemented with between 5 and 20% (v/v) foetal calf serum. The growth rate of the cells was essentially the same in all media (doubling time of 14.6 hours ±2.5) but growth was maintained for a longer period of time in 15 and 20% foetal calf serum.

A seeding density of $1 \times 10^5$ cells/ml is recommended for optimal growth although lower seeding densities can be employed but result in a longer lag phase of growth. Subculturing should be effected every 2-3 days.

EXAMPLE 2

In Vivo Culturing of Cell Lines

2A:RF-HBs-1

20 six week old Balb/c mice were primed with an intraperitoneal injection of 0.5 ml pristane (2,6,10,14-tetramethyl-pentadecane) at day 1 and day 7. At day 14 each mouse was implanted intraperitoneally with $1 \times 10^6$ viable hybridoma RF HBs-1 cells. 10 days following implantation all the mice were showing signs of massive tumour growth and were sacrificed, and the ascites fluid collected via a 19 gauge needle. The ascites fluid was centrifuged at 2000 g and the clear supernatants containing RF-HBs-1 antibody collected and stored at $-20°$ C.

2B:RF-HBs-2.

Balb/c mice were primed with 2 intraperitoneal injections of 0.5 ml pristane given at 2, one-week intervals prior to implantation of RF-HBs-2 cells. Each mouse was then implanted with $4 \times 10^5$ viable RF-HBs-2 cells and produced ascites tumours. After 20-25 days, when the mice had produced maximum yield of ascitic fluid, they were sacrificed and their ascitic fluid was found to contain approximately 20mg/ml protein of which 150 μg/ml is pure RF-HBs-2 antibody.

2C:RF-HBs-4.

Balb/c mice were primed with 2 intraperitoneal injections of 0.5 ml pristane given at 2, one-week intervals prior to implantation of RF-HBs-4 cells. Each mouse was then implanted with $5 \times 10^5$ viable RF-HBs-4 cells and produced ascites tumours After 15-20 days the mice had produced maximum yield of ascitic fluid found to contain 180 μg/ml RF-HBs-4 antibody.

EXAMPLE 3

Coating of Polystyrene Beads with RF-HBs-1, RF-HBs-2 and RF-HBs-4 Monoclonal Antibodies Polystyrene beads were coated with each of the three monoclonal antibodies in the form of ascitic fluid at various dilutions in pH 9.6 bicarbonate buffer (0.015M $Na_2CO_3$:0.035M $NaHCO_3$) by incubating for 1 hour, at 20° C. with agitation, followed by at least 16 hours incubation at 4° C. in the same antibody-buffer mixtures The beads were then washed and incubated for 4 hours, at room temperature, with 200 µl $^{125}$I HBs-Ag (Abbott Laboratories) to determine the optimum coating conditions (see Table 1 below).

TABLE 1

| Dilution of ascitic fluid | cpm | | |
|---|---|---|---|
| | RF-HBs-1 | RF-HBs-2 | RF-HBs-4 |
| 1:10 | 12,500 | — | — |
| 1:25 | — | 4143 | — |
| 1:50 | 15,100 | 9420 | 7275 |
| 1:100 | 17,900 | 9134 | 7667 |
| 1:200 | — | 8399 | 8806 |
| 1:400 | — | 8521 | 6717 |
| 1:1000 | 6090 | — | — |

The pH of 9.6 for the coating buffer used in this Example has been found to be optimal. Furthermore, when coating ads with combinations of monoclonal antibodies, the antibodies will normally be added to the beads together, since sequential addition of the monoclonals to the beads gives no improvement.

The beads, once coated with antibody can be dried, following 3 washes with distilled water, by centrifugation over an absorbant pad. These beads will remain stable at −20° C. for at least 3 months.

EXAMPLE 4

Recognition of HBs-Ag by the three monoclonals

The monoclonal antibody produced by the cell line RF-HBs-1 recognises an epitope that is common to the ad and ay subtypes of HBsAg and that is different from the epitopes of HBsAg recognised by the RF-HBs-2 and -4 antibodies, as is illustrated in the following competition binding study.

Polystyrene beads coated with HBsAg of mixed subtype (AUSAB: Abbott Laboratories) were incubated overnight at room temperature with 50 µg/ml of either Protein A-purified RF-HBs-1, RF-HBs-2 or RF-HBs-4 antibodies, or with an equivalent titre of horse antiserum to HBs-Ag, and then for a further four hours at room temperature with $^{125}$I-RF-HBs-1 or $^{125}$I-RF-HBs-2 antibody, iodinated as described in Example 5 (100,000 cpm), The results are given in Table 2 below.

TABLE 2

| Blocking antibody | Percentage binding | |
|---|---|---|
| | $^{125}$I-RF-HBs-1 | $^{125}$I-RF-HBs-2 |
| 50 µg/ml RF-HBs-1 | 52% | 120% |
| 50 µg/ml RF-HBs-2 | 110% | 26% |
| 50 µg/ml RF-HBs-4 | 111% | — |
| Horse anti-serum to HBsAG (at equivalent titre) | 70% | — |
| Control (50% NBCS) | 100% | 100% |

The results show that, whereas RF-HBs-1 and RF HBs-2 antibodies inhibit their own binding, there is no inhibition of binding by the other antibodies. Horse anti-serum did, on the other hand, inhibit RF-HBs-1 antibody binding.

EXAMPLE 5

Use of Cell Line Antibodies in Radiometric assay

RF-HBs-1 antibody was purified from ascitic fluid from mice implanted with the RF-HBs-1 cell line by elution at pH 5.5 from a protein A-Sepharose column (Pharmacia Fine Chemicals, Uppsala, Sweden) according to the method of Prowse & Jenkin (Immunochemistry 15 425–436, 1978.) 5µg of RF-HBs-1 antibody purified in this way, were iodinated with 0.5 mCi $^{125}$I using 2.5 µg Chloramine T in a total reaction volume of 15 µl, incubating for 30 seconds at 4° C., so as to give an equimolar binding ratio of $^{125}$I to antibody. (RF-HBs-2 and -4 antibodies were similarly purified and iodinated).

Polystyrene beads coated with RF-HBs-1, RF-HBs-2, RF-HBs-4 or combinations of these monoclonal antibodies, or Ausria II beads, were incubated with 200 µl of either HBsAg −ve human serum or with 200 µl of human serum containing 20 ng/ml HBsAg, for 2 hours, at 45°, washed and incubated for a further 1 hour at 45° with $^{125}$I-RF-HBs-1, $^{125}$I-RF-HBs-2 or $^{125}$I-RF-HBs-4 (approx. 100,000 cpm per assay), washed and counted. Results are expressed either as cpm (means of at least 2 samples) or as the ratio between the counts obtained with the HBsAg +ve sample and the HBsAg −ve sample (+/−).

TABLE 3

| Solid phase | HBsAg | Tracer | | | | | | | |
|---|---|---|---|---|---|---|---|---|---|
| | | RF-HBs-1 | | RF-HBs-2 | | RF-HBs-4 | | AUSRIA II | |
| | | CPM | +/− | CPM | +/− | CPM | +/− | CPM | +/− |
| RF-HBs-1 | + | 694 | 21 | 167 | 2.6 | | | 1723 | 27 |
| | − | 33 | | 65 | | | | 64 | |
| RF-HBs-2 | + | 1473 | 70 | | | | | | |
| | − | 21 | | | | | | | |
| RF-HBs-4 | + | 1487 | 45 | | | | | | |
| | − | 33 | | | | | | | |
| RF-HBs-1 + RF-HBs-2 | + | 2287 | 51 | | | | | | |
| | − | 45 | | | | | | | |
| RF-HBs-1 + RF-HBs-2 + RF-HBs-4 | + | 1370 | 76 | | | 742 | 3.7 | | |
| | − | 18 | | | | 198 | | | |
| RF-HBs-2 + RF-HBs-4 | + | 2009 | 52 | | | | | | |
| | − | 39 | | | | | | | |
| AUSTRIA II | + | 1393 | 19.6 | 176 | 2.2 | | | 3445 | 59 |
| | − | 71 | | 81 | | | | 58 | |

This Table shows that the highest +/− ratio and hence the most sensitive assay was obtained when all three monoclonals were used in the solid-phase with $^{125}$I-RF-HBs-1 as tracer.

EXAMPLE 6

Limits of Detection of HBsAg

Polystyrene beads, coated with optimal concentrations of either RF-HBs-1, RF-HBs-2 or RF-HBs-4 monoclonal antibodies or with combinations of these antibodies were incubated for 2 hours, at 45° C., with 200 μl of either HBsAg −ve human serum or with 200 μl of human serum containing known amounts of HBsAg, washed and incubated with 200 μl $^{125}$I-RF-HBs-1 (200,000 cpm per assay) for a further one hour at 45° C.

The results are given in Table 4 below which also gives results of a similar titration of HBsAg using an AUSRIA II RIA. Results are expressed both as cpm (mean of at least 2 experiments) or as +/− ratios.

TABLE 4

| HBsAg (ng/ml) | Tracer Solid-phase | RF-HBs-1 | | RF-HBs-2 | | RF-HBs-4 | | RF-HBs-1 + RF-HBs-2 | | RF-HBs-2 + RF-HBs-4* | | RF-HBs-1 + RF-HBs-2 + RF-HBs-4 | | AUSRIA II | |
|---|---|---|---|---|---|---|---|---|---|---|---|---|---|---|---|
| | | cpm | +/− | cpm | +/− | cpm | +/− | cpm | +/− | cpm | +/− | cpm | +/− | cpm | +/− |
| 20 | | 510 | 7.3 | 1472 | 70 | 2278 | 18 | 2287 | 51 | 6011 | 103 | — | — | 4197 | 35 |
| 10 | | 207 | 3.0 | 701 | 33 | 759 | 6.0 | 601 | 13 | 1958 | 33.6 | 200 | 12 | 1188 | 9.8 |
| 5 | | 149 | 1.7 | 343 | 16 | 513 | 4.1 | 336 | 7.5 | 1012 | 17.3 | 107 | 6.7 | 500 | 4.1 |
| 2.5 | | 87 | 1.2 | 181 | 8.6 | 336 | 2.7 | 267 | 5.9 | 450 | 7.7 | 44 | 2.8 | 230 | 1.9 |
| 1.25 | | 62 | 1.0 | 137 | 6.5 | 220 | 1.7 | 204 | 4.5 | 171 | 2.9 | 32 | 2.0 | — | — |
| 0.6 | | — | — | 100 | 4.8 | 168 | 1.3 | 201 | 4.4 | 152 | 2.6 | 22 | 1.4 | — | — |
| 0.3 | | — | — | 36 | 1.7 | 129 | 1.0 | — | — | 77 | 1.3 | 18 | 1.1 | 150 | 1.2 |
| 0.15 | | — | — | 29 | 1.4 | — | — | — | — | — | — | 16 | 1.0 | — | — |
| 0.075 | | — | — | 19 | <1 | — | — | — | — | — | — | — | — | — | — |
| 0 | | 61 | — | 21 | — | 126 | — | 44 | — | 58 | — | 16 | — | 121 | — |

*Incubation conditions: 4 hours at 20° C. followed by 2 hours at 20° C.

EXAMPLE 7

Detection of HBsAg positive samples by the three monoclonals

200 μl aliquots of 300 samples of human serum, shown to be HBsAg +ve or HBsAg −ve by either AUSRIA II RIA or by Hepatest (253 +ve; 47 −ve) were incubated for 2 hours, at 45° C. with polystyrene beads coated with either RF-HBs-2 or RF-HBs-4 monoclonal antibodies or with a mixture of RF-HBs-1, RF-HBs-2 and RF-HBs-4 antibodies. After washing, the beads were incubated for a further 1 hour at 45° C. with $^{125}$I-RF-HBs-1 (200,000 cpm per assay), washed and counted.

As shown in Table 5 below, of the 253 HBs-Ag-positive samples, 219 were positive with RF-HBs-2 antibody but 34 were negative. However, all of those 34 samples that were shown to be HBsAg-positive, but unreactive with RF-HBs-2 antibody, gave positive values when assayed with RF-HBs-4 antibody used as solid phase. Similarly, of the 253 HBsAg +ve samples tested, 10 were undetected by RF-HBs-4 antibody when used alone as a solid-phase, but these 10 all gave positive values when assayed with RF-HBs-2 antibody used as solid phase.

TABLE 5

| Number of samples | AUSRIA II/ Hepatest | RF-HBs-2 | RF-HBs-4 | RF-HBs-1 + RF-HBs-2 + RF-HBs-4 |
|---|---|---|---|---|
| 209 | + | + | + | + |
| 34 | + | − | + | + |
| 10 | + | + | − | + |
| 47 | − | − | − | − |

EXAMPLE 8

Two-stage Radiometric Assay for HBsAg

Polystyrene beads coated with RF-HBs-1, RF-HBs-2 and RF-HBs-4 were incubated for various times, at 20, 37 or 45° C. with 200 μl human serum containing 5 μg/ml HBsAg or with 200 μl MBsAg −ve human serum. The beads were washed and incubated for further times at 20, 37 or 45° C. with $^{125}$I-RF-HBs-1 tracer, washed and counted.

TABLE 6

| Time of 1st incubation in hours | Time of 2nd incubation in hours | +/− count ratio | | |
|---|---|---|---|---|
| | | 20° C. | 37° C. | 45° C. |
| 4 | 1 | 463 | 289 | 227 |
| 4 | 2 | 643 | 475 | 329 |
| 4 | 4 | 559 | 280 | 213 |
| 8 | 16 | 352 | 395 | 453 |
| 1 | 4 | 226 | 182 | 378 |
| 2 | 4 | 435 | 272 | 229 |
| 4 | 4 | 559 | 280 | 213 |
| 16 | 4 | 719 | 286 | 453 |

Recommended incubation times for a two-stage RF-HBs-monoclonal antibody assay for HBsAg are thus as follows:

1st incubation of serum with monoclonal antibody-coated beads:
  either 4 hours at room temperature or 16 hours at room temperature
2nd incubation of washed beads with RF-HBs-1 tracer:
  2 hours at room temperature.

EXAMPLE 9

One-stage Radiometric assay for HBsAg

Polystyrene beads coated with RF-HBs-2 and RF-HBs-4 antibodies (1:200 dilutions of ascitic fluid) were incubated for various times at 20° C. with 200 μl of either HBsAg −ve human serum or with human serum containing 20 ng/ml HBsAg and with 10 μl $^{125}$I-RF-HBs-1 (100,000 cpm per assay), washed and counted. Results are expressed as cpm (mean of two separate experiments) or as the ratio between the counts obtained with the HBsAg +ve and HBsAg −ve samples.

TABLE 7

| Incubation time (hours) | cpm HBsAg + ve | cpm HBsAg − ve | +/− count ratio |
|---|---|---|---|
| 2 | 1470 | 14 | 105 |
| 4 | 2026 | 23 | 88 |
| 5 | 2563 | 20 | 128 |

Coincubation of bead, sample and tracer as in this Example gives better results than if the bead and sample are preincubated and the results are little different from those obtained if the tracer and sample are preincubated.

This one-stage assay is possible since the antibodies are monoclonal which, unlike conventional antisera, do not compete for antigenic binding sites, and is an attractive system for use where very rapid screening methods for HBs-Ag are required e.g. in Blood Transfusion Centres and in Blood Products Laboratories, since it involves fewer manipulations than a two-stage assay. This assay can be carried out within 2 hours without apparent loss of sensitivity.

EXAMPLE 10

Use of RF-HBs-1 antibody in affinity chromatography of HBsAg.

RF-HBs-1 antibody, partially purified from ascitic fluid by ammonium sulphate precipitation, was coupled to CnBr-S4B (Pharmacia Fine Chemicals, Uppsala, Sweden) according to the manufacturers instructions. 100 ml of human serum containing HBsAg were passed down this column, resulting in a 98.7% removal of the HBsAg from the serum. In addition, 100% of the removed antigen could be eluted from the column using 3M KI. The antigen was immunogenic in mice and rabbits and was shown to be free from other human serum contaminants by immunoelectrophoresis against a rabbit antiserum to whole serum.

EXAMPLE 11

Use of RF-HBs-1 antibody in the localisation of HBsAg in cellular material

RF-HBs-1 antibody in supernatants from cultures of RF-HBs-1 cells was used to identify HBsAg in frozen sections of liver biopsies from HBV-bearing humans or chimpanzees or in cells bearing the virus, visualising the antigen-antibody complex with a goat antiserum to mouse immunoglobulin, coupled to a fluorescent molecule. Furthermore, Protein A-purified RF-HBs-1 antibody was conjugated to biotin by incubation of 1 mg of RF-HBs-1 antibody in 1 ml of pH 8.3 bicarbonate-saline buffer (0.1M NaHCO$_3$:0.5M NaCl) for 4 hours, at 20° C., with 90 µg biotin succinamide dissolved at 1 mg/ml in DMSO. Following an overnight dialysis at 4° C., against phosphate-buffered saline, the RF-HBs-1 antibody-biotin conjugate was used, in combination with an avidin-fluorochrome conjugate or with avidin-ferritin, to visualise HBsAg by immunofluorescent microscopy and by immuno-electron microscopy, respectively.

We claim:

1. A monoclonal antibody to hepatitis B surface antigen which is secreted by hybridoma cell line RF-HBs-1.

2. An antibody according to claim 1 substantially free from other immunological material.

3. A composition comprising a monoclonal antibody as claimed in claim 1 or 2 and a carrier or diluent.

4. A composition according to claim 3 in which the carrier is a plastics substrate onto which are coated RF-HBs-1, antibody and monoclonal antibodies to hepatitis B surface antigen secreted by hybridoma cell lines RFHBs-2 and RF-HBs-4.

5. A composition according to claim 3 in which the carrier is a plastics substrate onto which are coated RF-HBs-1 antibody and a monoclonal antibody to hepatitis B surface antigen secreted by a hybridoma cell line selected form the group consisting of RF-HBs-2 and RF-HBs-4.

6. A process of producing monoclonal antibodies to hepatitis B surface antigen which comprises culturing hybridoma cell line RF-HBs-1, and recovering the antibodies produced.

7. A process according to claim 6 in which the cell line is cultured in vitro in a nutrient culture medium therefor and the antibodies are recovered from culture supernatant.

8. A process according to claim 6 in which the cell line is established as an ascites tumour in a mouse by implanting the cell line and the antibodies are recovered from ascites fluid or serum of the mouse.

9. A method of diagnosing the presence of hepatitis B surface antigen in a biological sample, said method comprising the steps of:
   contacting said antigen with antibodies secreted by hybridoma cell line RF-HBs-1; and
   detecting the presence of said antigen by immunofluorescent microscopy or immuno-electron microscopy or in a solid-phase radiometric assay system or in an enzyme-linked immunoassay.

10. A method according to claim 9 which comprises incubating a serum sample taken form a human or animal with RF-HBs-1 antibody and one or more other monoclonal antibodies which recognise hepatitis B surface antigen, in the solid phase, washing the solid phase and incubating it with radio-labelled or enzyme-labelled RF-HBs-1 antibody as tracer.

11. A method according to claim 10 in which the serum sample is incubated with RF-HBs-1, antibody and monoclonal antibodies to hepatitis B surface antigen secreted by hybridoma cell lines RF-HBs-2 and RF-HBs-4, said antibodies being in the solid phase.

12. A method according to claim 9 which comprises incubating a serum sample taken from a human or animal with RF-HBs-2 and RF-HBs-4 antibodies in the solid-phase and, as tracer, radio-labelled or enzyme-labelled RFHBs-1 antibody, without an intermediate washing step.

13. A method according to claim 10 in which the serum sample is incubated with RF-HBs-1 antibody and a monoclonal antibody to hepatitis B surface antigen secreted by a hybridoma cell line selected form the group consisting of RF-HBs-2 and RF-HBs-4, said antibodies being in the solid phase.

14. A method of isolating hepatitis B surface antigen from a biological sample which comprises contacting the biological sample with RF-HBs-1, antibody and optionally with RF-HBs-2 and/or RF-HBs-4 antibodies in the solid phase to cause hepatitis B surface antigen to being to the antibodies and subsequently separating the hepatitis B surface antigen material form the solid phase.

15. A kit comprising a fits container which contains a plastics substrate coated with either (1) RF-HBs-1 antibody and one or more other monoclonal antibodies which recognise hepatitis B surface antigen, or (2) with monoclonal antibodies to hepatitis B surface antigen secreted hybridoma cell lines RF-HBs-2 and RF-HBs-4, and a second container which contains antibody secreted by hybridoma cell line RF-HBs-1 to which antibody a radio-label or enzyme label has been attached.

16. A kit according to claim 15 in which the substrate is coated with RF-HBs-1, antibody and monoclonal antibodies to hepatitis B surface antigen secreted by hybridoma cell lines RF-HBs-2 and RF-HBs-4.

17. A kit according to claim 15 in which the substrate is coated with RF-HBs-1 antibody and a monoclonal antibody to hepatitis B surface antigen secreted by a hybridoma cell line selected from the group consisting of RF-HBs-2 and RF-HBs-4.

18. Hybridoma cell line RF-HBs-1 which secretes a monoclonal antibody to hepatitis B surface antigen.

19. The cell line RF-HBs-1, according to claim 18 substantially free from other cellular material.

20. A process of propagating a hybridoma cell line as claimed in claim 18 or 19 in vitro which comprises culturing the cell line in a nutrient culture medium therefor.

21. A process of propagating a hybridoma cell line as claimed in claim 18 or 19 in vivo which comprises implanting the cell line into a mouse to establish an ascites tumour.

22. A composition comprising a hybridoma cell line as claimed in claim 18 or 19 and a nutrient medium capable of maintaining the cell line.

23. A kit according to claim 15 or 16 or composition according to claim 8 in which the plastics substrate is of polystyrene in the form of beads, sticks or tubes.

24. A kit comprising a first container which contains a plastics substrate coated with either (1) RF-HBs-1 antibody and one or more other monoclonal antibodies which recognise hepatitis B surface antigen, or (2) with a monoclonal antibody to hepatitis B surface antigen secreted by a hybridoma cell line selected form the group consisting of RF-HBs-2 and RF-HBs-4, and a second container which contains antibody secreted by hybridoma cell line RF-HBs-1 to which antibody a radio-label or enzyme label has been attached.

* * * * *